US00PP25617P2

(12) United States Plant Patent
Wain

(10) Patent No.: US PP25,617 P2
(45) Date of Patent: Jun. 9, 2015

(54) ***CHRYSANTHEMUM* PLANT NAMED 'FIMMDAYAPPLEBLOS'**

(50) Latin Name: *Chrysanthemum×morifolium*
Varietal Denomination: Fimmdayappleblos

(71) Applicant: Peter Wain, Locks Heath (GB)

(72) Inventor: Peter Wain, Locks Heath (GB)

(73) Assignee: FIDES B.V., De Lier (NL)

( * ) Notice: Subject to any disclaimer, the term of this patent is extended or adjusted under 35 U.S.C. 154(b) by 89 days.

(21) Appl. No.: 13/987,343

(22) Filed: Jul. 15, 2013

(51) Int. Cl.
*A01H 5/00* (2006.01)

(52) U.S. Cl.
USPC ..... Plt./287

(58) Field of Classification Search
USPC ..... Plt./287
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'Fimmdayappleblos', characterized by its upright to outwardly spreading and uniformly mounded plant habit; freely branching habit; dense and full plant habit; uniform and freely flowering habit; medium-size decorative-type inflorescences with light purple and white-colored ray florets; early flowering habit; and good garden performance.

1 Drawing Sheet

Botanical designation: *Chrysanthemum×morifolium.*
Cultivar denomination: 'FIMMDAYAPPLEBLOS'.

BACKGROUND OF THE INVENTION

The present invention relates to a new and distinct *Chrysanthemum* plant, botanically known as *Chrysanthemum×morifolium*, commercially grown as a garden *Chrysanthemum* and hereinafter referred to by the name 'Fimmdayappleblos'.

The new *Chrysanthemum* plant is a product of a planned breeding program conducted by the Inventor in Fareham, Hampshire, United Kingdom. The objective of the breeding program is to create new early-flowering garden *Chrysanthemum* plants with numerous attractive inflorescences.

The new *Chrysanthemum* plant originated from a cross-pollination made in January, 2008 by the Inventor in Fareham, Hampshire, United Kingdom of a proprietary selection of *Chrysanthemum×morifolium* identified as code number 83279, not patented, as the female, or seed, parent with a proprietary selection of *Chrysanthemum×morifolium* identified as code number 83339, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2008.

Asexual reproduction of the new *Chrysanthemum* by terminal vegetative cuttings was first conducted in Fareham, Hampshire, United Kingdom in December, 2008. Asexual reproduction by terminal vegetative cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fimmdayappleblos'. These characteristics in combination distinguish 'Fimmdayappleblos' as a new and distinct *Chrysanthemum* plant:

1. Upright to outwardly spreading and uniformly mounded plant habit.
2. Freely branching habit; dense and full plant habit.
3. Uniform and freely flowering habit.
4. Medium-size decorative-type inflorescences with light purple and white-colored ray florets.
5. Early flowering habit, under natural season conditions, plants flower the second week in August in the United Kingdom.
6. Good garden performance.

Plants of the new *Chrysanthemum* can be compared to plants of the female parent selection. Plants of the new *Chrysanthemum* differ from plants of the female parent selection, in the following characteristics:

1. Under natural season conditions, plants of the new *Chrysanthemum* flower earlier than plants of the female parent selection.
2. Plants of the new *Chrysanthemum* have larger inflorescences than plants of the female parent selection.
3. Plants of the new *Chrysanthemum* and the female parent selection differ in ray floret color as plants of the female parent selection have darker pink-colored ray florets.

Plants of the new *Chrysanthemum* can be compared to plants of the male parent selection. Plants of the new *Chrysanthemum* differ from plants of the male parent selection, in the following characteristics:

1. Under natural season conditions, plants of the new *Chrysanthemum* flower earlier than plants of the male parent selection.
2. Plants of the new *Chrysanthemum* have slightly smaller inflorescences than plants of the male parent selection.

3. Plants of the new *Chrysanthemum* and the male parent selection differ in ray floret color as plants of the male parent selection have white-colored ray florets.

Plants of the new *Chrysanthemum* can be compared to plants of *Chrysanthemum×morifolium* 'Yogigi', not patented. In side-by-side comparisons conducted in Fareham, Hampshire, United Kingdom, plants of the new *Chrysanthemum* differed from plants of 'Yogigi' in the following characteristics:

1. Under natural season conditions, plants of the new *Chrysanthemum* flowered earlier than plants of 'Yogigi'.
2. Plants of the new *Chrysanthemum* had larger inflorescences than plants of 'Yogigi'.
3. Plants of the new *Chrysanthemum* and 'Yogigi' differed in ray floret color as plants of 'Yogigi' had white-colored ray florets.

BRIEF DESCRIPTION OF THE PHOTOGRAPH

The accompanying photograph illustrates the overall appearance of the new *Chrysanthemum* showing the colors as true as it is reasonably possible to obtain in colored reproductions of this type. Colors in the photograph may differ slightly from the color values cited in the detailed botanical description which accurately describe the colors of the new *Chrysanthemum.*

The photograph comprises a top perspective view of a typical flowering plant of 'Fimmdayappleblos' grown in a container.

DETAILED BOTANICAL DESCRIPTION

The aforementioned photograph and following observations and measurements describe plants grown during the winter in 14-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were pinched one time and were about twelve weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum×morifolium* 'Fimmdayappleblos'.

Parentage:

*Female, or seed, parent.*—Proprietary selection of *Chrysanthemum×morifolium* identified as code number 83279, not patented.

*Male, or pollen, parent.*—Proprietary selection of *Chrysanthemum×morifolium* identified as code number 83339, not patented.

Propagation:

*Type.*—Terminal vegetative cuttings.

*Time to initiate roots, summer.*—About ten days at temperatures of about 21° C.

*Time to initiate roots, winter.*—About twelve days at temperatures of about 21° C.

*Time to produce a rooted young plant, summer.*—About three weeks at temperatures of about 21° C.

*Time to produce a rooted young plant, winter.*—About four weeks at temperatures of about 21° C.

*Root description.*—Fine, fibrous; light brown in color.

*Rooting habit.*—Freely branching; medium density.

Plant description:

*Plant and growth habit.*—Herbaceous decorative-type garden *Chrysanthemum*; stems upright to outwardly spreading giving a uniformly mounded appearance to the plant; numerous lateral branches and relatively short internodes, dense and full plant habit; moderately vigorous growth habit.

*Plant height.*—About 13 cm.

*Plant width.*—About 19.5 cm.

*Branching habit.*—Freely branching habit, about six lateral branches develop after removal of terminal apex (pinching); each primary lateral with numerous secondary and tertiary lateral branches.

*Lateral branches.*—Length: About 9 cm. Diameter: About 3 mm. Internode length: About 5 mm. Strength: Strong, brittle. Aspect: About 75° from stem bending upwardly. Texture: Fine pubescence. Color: Close to 146B.

*Leaves.*—Arrangement: Alternate, simple. Length: About 5.5 cm. Width: About 4.2 cm. Shape: Palmately-lobed; roughly ovate with three to five lobes. Apex: Broadly acute to slightly emarginate. Base: Attenuate to truncate. Margin: Palmately lobed, sinuses between lateral lobes parallel to divergent; dentate. Texture, upper and lower surfaces: Fine pubescence; veins prominent on lower surface. Color: Developing leaves, upper surface: Close to 144A. Developing leaves, lower surface: Close to 138B. Fully expanded leaves, upper surface: Close to N137D; venation, close to 148B. Fully expanded leaves, lower surface: Close to 147B; venation, close to 148C. Petioles: Length: About 1.5 cm. Diameter: About 2 mm. Texture, upper and lower surfaces: Fine pubescence. Color, upper surface: Close to 137C. Color, lower surface: Close to 148C.

Inflorescence description:

*Form and flowering habit.*—Decorative-type inflorescence form with oblanceolate-shaped ray florets; inflorescences borne on terminals above and beyond the foliar plane; disc and ray florets arranged acropetally on a capitulum; freely flowering habit with 90 inflorescences developing per plant.

*Fragrance.*—Mildly fragrant; pungent, herbaceous.

*Flowering response.*—Early flowering habit, plants exposed to natural season conditions begin flowering the second week of August in the United Kingdom.

*Inflorescence longevity.*—Inflorescences maintain good color and substance for about three to five weeks on the plant; inflorescences persistent.

*Inflorescence buds.*—Height: About 4 mm. Diameter: About 6 mm. Shape: Oblate. Color: Close to 144B.

*Inflorescence height.*—About 1.3 cm.

*Inflorescence diameter.*—About 4 cm.

*Disc diameter.*—About 7 mm.

*Receptacles.*—Height: About 4 mm. Diameter: About 4 mm. Shape: Ovoid. Color: Close to 145C.

*Ray florets.*—Orientation: Initially upright, then about 40° to 85° from vertical bending upwardly. Length: About 2.3 cm. Width: About 7 mm. Shape: Oblanceolate. Apex: Emarginate to praemorse. Base: Fused into a short tube. Margin: Entire. Texture, upper and lower surfaces: Smooth, glabrous. Number of ray florets per inflorescence: About 72 arranged in about four whorls. Color: When opening, upper surface: Close to 70B; towards the base, close to NN155C.

When opening, lower surface: Close to N155B; towards the base, close to NN155C; towards the apical margin, close to 72C. Fully opened, upper surface: Close to N78C; towards the base, close to NN155C; color becoming closer to N78D with development. Fully opened, lower surface: Close to N155B; towards the base, close to NN155C; towards the apical margin, close to 72C.

*Disc florets*.—Shape: Tubular, elongated. Length: About 6 mm. Diameter: About 1 mm. Number of disc florets per inflorescence: About 46 massed at the center of the inflorescence. Color, immature and mature: Apex: Close to 9B. Mid-section: Close to 144D. Base: Close to NN155C.

*Phyllaries*.—Number of phyllaries per inflorescence: About 15 arranged in about three to five whorls. Length: About 7 mm. Width: About 3 mm. Shape: Lanceolate. Apex: Acute to obtuse. Base: Truncate, fused. Margin: Entire. Texture, upper surface: Smooth, glabrous. Texture, lower surface: Fine pubescence. Color, upper surface: Close to 143B. Color, lower surface: Close to 143C.

*Peduncles*.—Length, terminal peduncle: About 2.5 cm. Diameter, terminal peduncle: About 2 mm. Angle: About 40° from vertical. Strength: Moderately strong; flexible. Texture: Fine pubescence. Color: Close to 139D.

*Reproductive organs*.—Androecium: None observed. Gynoecium (observed on ray florets only): Pistil length: About 5 mm. Stigma shape: Bi-parted. Stigma color: Close to 5B. Style length: About 4 mm. Style color: Close to 1C. Ovary color: Close to NN155C.

*Seeds and fruits*.—Seed and fruit production has not been observed on plants of the new *Chrysanthemum*.

Disease & pest resistance: Resistance to pathogens and pests common to *Chrysanthemum* plants has not been observed on plants of the new *Chrysanthemum*.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fimmdayappleblos' as illustrated and described.

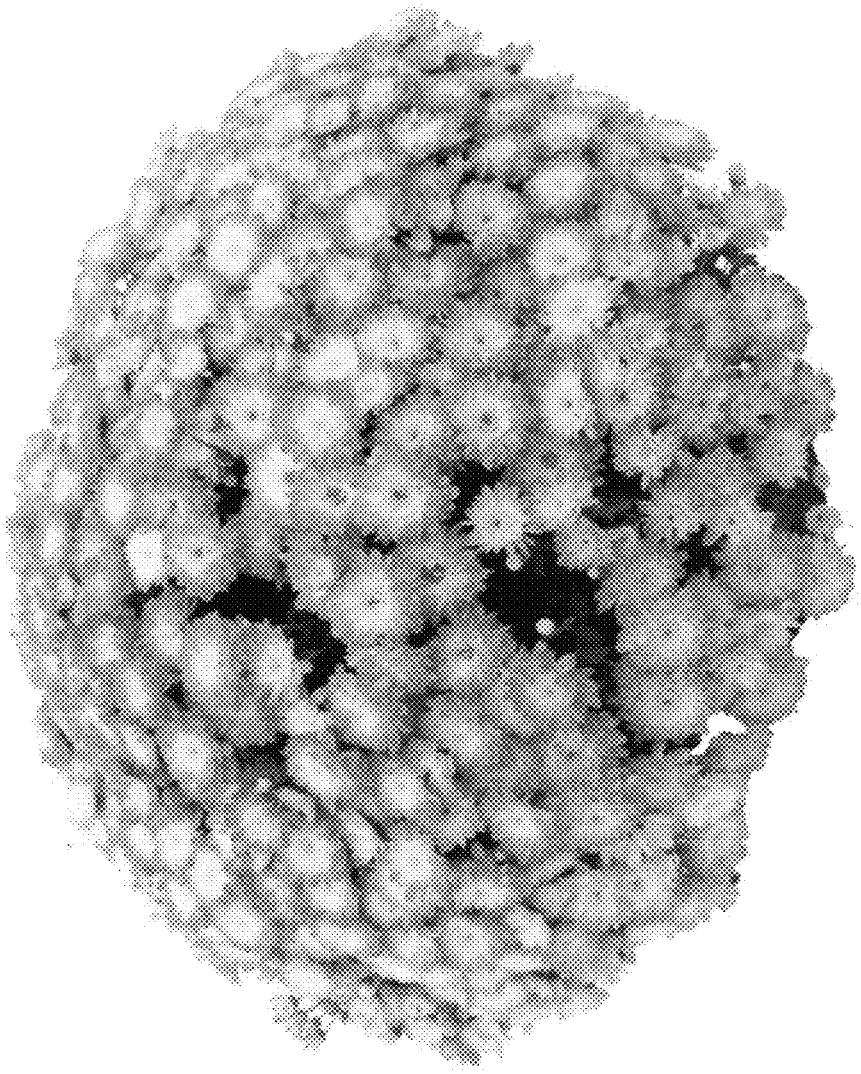

* * * * *